United States Patent
Meyer et al.

[11] Patent Number: 5,886,158
[45] Date of Patent: Mar. 23, 1999

[54] METAL COMPLEXES OF POLYAMINO OXIDES, AND THEIR UTILIZATION IN DIAGNOSTIC IMAGING

[75] Inventors: Dominique Meyer, Saint Maur; Olivier Rousseaux, Senlis; Michel Schaefer, Lagny; Christian Simonot, Paris, all of France

[73] Assignee: Guerbet S.A., Villepinte, France

[21] Appl. No.: 981,022

[22] PCT Filed: Jun. 25, 1996

[86] PCT No.: PCT/FR96/00992

§ 371 Date: Dec. 29, 1997

§ 102(e) Date: Dec. 29, 1997

[87] PCT Pub. No.: WO97/01359

PCT Pub. Date: Jan. 16, 1997

[30] Foreign Application Priority Data

Jun. 29, 1995 [FR] France ................... 95 07 860

[51] Int. Cl.$^6$ .................................. C07F 5/00
[52] U.S. Cl. ..................... 534/16; 534/10; 424/9.3; 424/9.4; 424/1.65
[58] Field of Search ..................... 424/1.11, 1.65, 424/1.81, 1.85, 9.1, 9.3, 9.4; 534/10–16

[56] References Cited

U.S. PATENT DOCUMENTS

| | | | |
|---|---|---|---|
| 5,324,504 | 6/1994 | Roger, Jr. et al. | 424/9.1 |
| 5,346,690 | 9/1994 | Gundersen et al. | 424/9.1 |
| 5,403,576 | 4/1995 | Lin et al. | 424/9.1 |

FOREIGN PATENT DOCUMENTS

| | | |
|---|---|---|
| 9316375 | 9/1993 | WIPO . |
| 9427644 | 12/1994 | WIPO . |

*Primary Examiner*—Jose' G. Dees
*Assistant Examiner*—Dameron Jomes
*Attorney, Agent, or Firm*—Jacobson, Price, Holman & Stern, PLLC

[57] ABSTRACT

The invention concerns gadolinium complexes of formula:

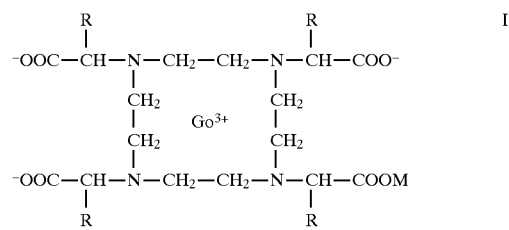

in which
R represents a group of formula:

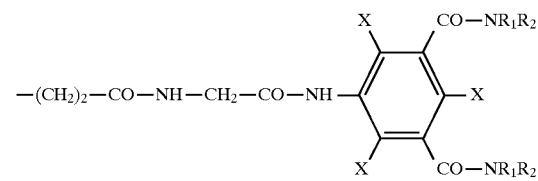

in which X is Br or I;
$R_1$ is H or optionally hydroxylated alkyl;
$R_2$ is hydroxylated alkyl; or
alternatively $R_1$ is H and $R_2$ is a group of formula:

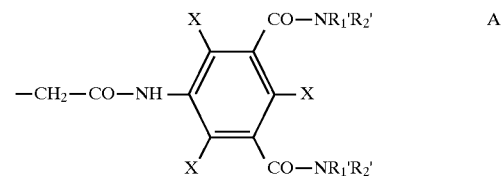

X being as defined above, and $R'_1$ and $R'_2$ being as defined for $R_1$ and $R_2$ excepted that they do not represent A, provided that —CO—$NR_1R_2$ or —CO—$NR'_1R'_2$ comprises at least 2 hydroxyl groups, and M represents H or the cation of an inorganic or organic base.

7 Claims, No Drawings

METAL COMPLEXES OF POLYAMINO OXIDES, AND THEIR UTILIZATION IN DIAGNOSTIC IMAGING

The present invention relates to metal complexes of polyamino acids, to a process for their preparation and to their use in diagnostic imaging.

These compounds are branched derivatives of gadoteric acid, which is sold in the form of the meglumine salt under the brand name Dotarem® as a contrast agent for magnetic resonance imaging. Meglumine gadoterate is a stable complex whose spin-lattice relaxivity at 37° C. and 20 MHz is about 3.5 $mM^{-1}s^{-1}$ which is of the same order of magnitude as that of the other commercial contrast agents.

The gadolinium complexes according to the invention have relaxivities $R_1$ greater than 20 $mM^{-1}s^{-1}$; this makes it possible to administer to an individual, in order to obtain the same signal intensity, a diagnostic, composition whose molar concentration of complexed $Gd^{3+}$, and thus of compound according to the invention, is 6 times and even 10 times as low as the concentrations currently used clinically.

Since the osmolality of the complex solutions of the invention, for the same relaxivity, is markedly lower than that of Dotarem® and even than that of nonionic compounds such as gadodiamide, it may be envisaged to use solutions whose weight content of active ingredient is greater than those which are known in order to obtain higher-quality images, without reaching an unacceptable level of side effects.

Besides the heavy metal ion $Gd^{3+}$, these complexes contain bromine or iodine atoms and are opaque to X-rays and they are sufficiently soluble, in particular owing to the presence of hydrophilic groups around the aromatic rings, to be used in conventional radiology or in dichromography.

The compounds of the invention have the formula:

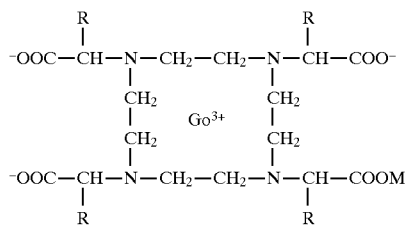

in which

R represents a group

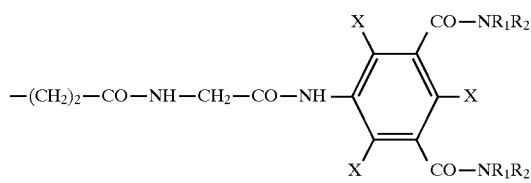

in which X is Br or I, $R_1$ is H, $(C_1-C_3)$alkyl or $(C_2-C_8)$mono- or polyhydroxyalkyl and $R_2$ is $(C_2-C_8)$mono- or polyhydroxyalkyl, or alternatively $R_1$ is H and $R_2$ is a group

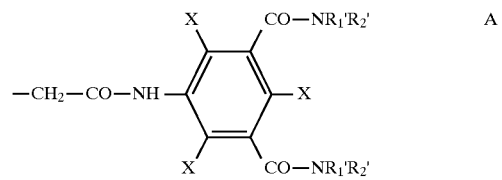

X being as defined above, and $R'_1$ and $R'_2$ taking, independently of each other, any one of the meanings given for $R_1$ and $R_2$, with the exception of A, provided that $-CO-NR_1R_2$ or $-CO-NR'_1R'_2$ comprises at least 2 hydroxyl groups, and M represents H or an organic or inorganic cation. Among the pharmaceutically acceptable cations, mention may be made of $Na^+$ or those derived from lysine, arginine, N-methylglucamine or diethanolamine.

The alkyl groups can be linear or branched.

Compounds in which $-CONR_1R_2$ or $-CONR'_1R'_2$ comprise at least 6 hydroxyl groups and more particularly represent $CON(CH_2(CHOH)_4CH_2OH)_2$ are preferred.

The compounds of formula I can be prepared by the action of the amine of formula II

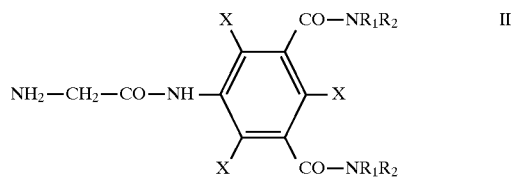

in which X, $R_1$ and $R_2$ are as defined above, on the gadolinium complex of formula III corresponding to the structural formula I in which $R=-(CH_2)_2COOH$, in the presence of a coupling agent, in particular one of those used in peptide synthesis, such as a carbodiimide, for example in aqueous solution.

The amines of formula II for which $R_2$ is different from A can be obtained by reacting $HNR_1R_2$ with the diacid dichloride of formula IV:

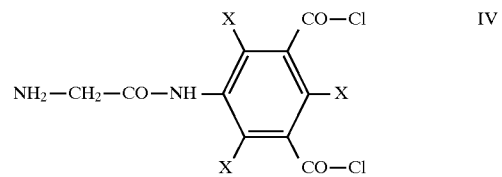

in which the $NH_2$ function is protected in the form of phthalimide, followed by a hydrazinolysis.

The amino alcohols $HNR_1R_2$ are known or can be prepared by methods similar to those described in the literature. Mention may be made, in particular, of commercial amino alcohols, defined by:

i) $R_1=H$ and $R_2=CH(CH_2OH)_2$;
ii) $R_1=H$ and $R_2=CH_2-CHOH-CH_2OH$ or $CH_2-(CHOH)_2-CH_2OH$;
iii) $R_1=CH_2(CHOH)_4CH_2OH$ and $R_2=CH_3$, $CH_2CH_2OH$ or $R_1$;
iv) glucosamine, and more generally those described in EP-A-558,395, EP-A-25,083 and EP-A-33,426.

The amines of formula II for which $R_2$ represents A and $R_1$ represents H are simply obtained by reacting an amine of formula $H_2NA$ with the diacid dichloride of formula IV which has been N-protected beforehand. It will be noted that the amine $H_2NA$, which corresponds to an amine of formula II in which $R_2$ is different from A, can be prepared in accordance with the process proposed above.

The contrast agent compositions for magnetic resonance imaging which comprise a compound of formula I in a pharmaceutically acceptable vehicle form another subject of the invention. Their pharmaceutical form will be adapted to the route of administration.

Preferably, these contrast agent compositions will be aqueous solutions of physiologically acceptable salts of the complex of formula I. The compositions of the invention can also contain stabilizers, various additives intended to make the solution isotonic or which allow its pH to be set, as well as any other type of additive commonly used in the art.

The concentration of the composition will be adapted to the route and site of administration; it will generally be between 0.01M and 0.5M, preferably between 0.05M and 0.1M.

The unit dose will, needless to say, depend on the structure of the complex and on the nature of the examination; in general, from 0.005 mmol/kg to 0.1 mmol/kg will be administered.

In the text hereinbelow, processes are described for the preparation of the complex of formula III, in aqueous solution, of the amine of formula II in which $R_1=R_2=CH_2(CHOH)_4CH_2OH$ and of that in which $R_1=H$ and $R_2=A$ with $R'_1=R'_2=CH_2(CHOH)_4CH_2OH$.

Preparation of the complex of formula III

Step a)

167 g of dimethyl 2-bromoglutarate are poured slowly into a suspension of 30g of 1,4,7,10-tetra-azacyclododecane and 97 g of potassium carbonate in 875 ml of acetonitrile; the mixture is stirred under an inert atmosphere at 60° C. for 48 hours, during which time 83 g of dimethyl 2-bromoglutarate are added. Next, at room temperature, the reaction medium is filtered and the solution concentrated to dryness. The residual oil is purified by chromatography on silica, eluting with a dichloromethane/methanol gradient (100/0 to 80/20) to give 43 g of octa ester in oil form.

Step b)

The above oil dissolved in 72 ml of methanol is introduced into an aqueous NaOH solution (68 g of NaOH; 340 ml of water) and the mixture is kept stirring at 70° C. for 48 hours.

The methanol is removed under reduced pressure and the aqueous phase extracted with methylene chloride, after which about 800 ml of Amberlite® cationic ion-exchange resin, sold by Rohm and Haas under the name IRC 50 (weak acid), are introduced.

After 1 hour of contact, the resin is removed and 680 ml of Amberlite® anionic ion-exchange resin, known as IRA 458 (strong base), are introduced into the solution.

After 12 hours, the resin is separated out and introduced into a column; the desired product is isolated by elution using 4 l of aqueous 3N acetic acid solution, followed by 4 l of 6N solution.

After removal of the solvent under reduced pressure, 31 g of white crystals are obtained.

$^{13}C$ NMR (200 MHz; DMSO-d6; T=30° C.): 24; 31; 48; 62; 172; 174.

Step c)

29.4 g of the octo acid obtained above are suspended in 530 ml of water with 15.8 g of $GdCl_3.6H_2O$; aqueous 1N NaOH solution is introduced slowly, with stirring, until the pH of the medium is stabilized at 6.5. The medium is then filtered through a Millipore® filter with a mesh size of 0.45 µm and the filtrate is concentrated to dryness. After drying, 49.3 g of sodium salt of the gadolinium complex of formula III are obtained in the form of a beige-coloured solid containing the NaCl formed during the complexation.

This product can be purified by precipitation from aqueous ethanol and processing, in order to remove the excess, non-complexed $Gd^{3+}$, using a chelating resin such as that sold by Biorad Laboratories under the brand name Chelex.

Relaxivity $R_1$ (37° C.; 20 MHz)=5.9 $mM^{-1}s^{-1}$;

Chromatography: HPLC on a Hibar Licrosorb® Diol 5 µm column, l=25 cm, d=4 mm; (Merck), $CH_3CN/0.01M$ $KH_2PO_4$ (50/50—v/v) as eluent Retention time: 2 minutes.

Preparation of the amine of formula II in which $R_1=R_2CH_2$—$(CHOH)_4$—$CH_2OH$ and X=I (Compound IIa)

Step a)

179 g of N-phthaloylglycine chloride are introduced portionwise, with stirring, into a solution, at 0° C., of 119 g of 5-amino-2,4,6-triiodoisophthaloyl dichloride in 500 ml of dimethylacetamide; the mixture is stirred for several hours at 0° C. and then overnight at room temperature and is introduced slowly into 10 litres of water; the precipitate formed is isolated and dissolved in 3 l of ethyl acetate. This solution is washed with aqueous sodium bicarbonate solution and then with water, dried and then concentrated. 125 g of 2,4,6-tri-iodo-5-phthalimidoacetamidoisophthaloyl dichloride are obtained.

Step b)

A solution of 104 g of the above acid dichloride, 208 g of disorbitylamine and 50 ml of triethylamine in 1000 ml of dimethylacetamide is maintained at 80° C. for 5 hours. The precipitate formed is separated out and the solvent is removed by distillation under reduced pressure; the residue is dissolved in water at pH 3 and placed in contact with 750 ml of Amberlite® cationic ion-exchange resin sold by Rohm and Haas under the name IRN 77 (strong acid). After stirring for 2 hours, the resin is separated out and 17 ml of hydrazine hydrate are introduced into the aqueous solution (700 ml) of the purified diamide. After stirring for 5 hours at 80° C., the medium is acidified at room temperature by addition of 26 ml of aqueous 10N hydrochloric acid solution. The precipitate formed is isolated and the solution is passed through a column of 500 ml of a weakly anionic ion-exchange resin (Amberlite® IRA 67) and then through 80 ml of weakly cationic resin (Amberlite® IRC 50); the solution obtained is treated with 4 l of Amberlite® strong acid resin, on which the final product becomes bound; it is eluted with aqueous $NH_4OH$ solution. The amine II is obtained in a yield of 70% in the form of a beige-coloured solid.

HPLC chromatography: LiChrosphere® 100 RP 18.5 µm column (Merck)–h=25 cm; d=4 mm.

Eluent*: $CH_3CN/PIC®$ B8 0.05M (Waters) 5/95;

flow rate: 1 ml/min

Retention time of the isomers: about 8 minutes

*: PIC B8: octanesulphonic acid/methanol/calcium acetate/water mixture.

Preparation of the amine of formula II in which $R_1=R_2=CH_2(CHOH)_4CH_2OH$ and X=Br (Compound IIb)

The same procedure as above is applied in order to obtain the desired product. The molecular peak of its mass spectrum by electrospray is correct. On high performance liquid chromatography, the retention times of the isomers are about 8 minutes under the same conditions as above.

The starting 5-amino-2,4,6-tribromoisophthalic acid is prepared in a yield of 85% by the action of 100 ml of bromine on a solution of 87 g of 5-amino-isophthalic acid in 1300 ml of water and 380 ml of concentrated hydrochloric acid.

TLC: Merck $SiO_2$:

$C_6H_6/CH_3COC_2H_5/HCO_2H$ (60/25/11) Rf=0.8;

$(CH_3)_2CHOH/CH_3COOC_2H_5/NH_4OH$ (35/35/40) Rf=0.4.

The corresponding acid dichloride is prepared in a conventional manner by the action of $SOCl_2$ on the corresponding diacid, in a yield of 88%.

TLC: Merck $SiO_2$:

$CH_2Cl_2$ Rf=0.9.

The phthalimides (acid dichloride and diamide) have respective retention times of 11 minutes and 15 to 30 minutes in high performance liquid chromatography, on a LiChrospher® 100 RP18, 5 μm column (Merck), l=250 mm; d=4 mm, with a flow rate of 1 ml/minute, eluting, in the first case, with a 60/40 mixture of acetonitrile and aqueous 0.01M $KH_2PO_4$ solution, and, in the second case, with the same mixture in proportions of 7/97 (v/v).

Preparation of the amine of formula II with $R_1$=H, $R_2$=A, $R'_1$=$R'_2$=$CH_2(CHOH)_4CH_2OH$, X=I (Compound IIc)

A solution of 59 g of 2,4,6-triiodo-5-phthalimidoacetamidoisophthaloyl dichloride, 200 g of the amine IIa obtained by carrying out the above procedure and 29.5 ml of tributylamine in 400 ml of dimethylacetamide is stirred for 24 hours at 70° C.

The solvent is then removed under reduced pressure and the residue is purified by chromatography on 4 kg of XAD 1600 adsorbent material (Rohm and Haas), eluting with a $CH_3OH/H_2O$ mixture.

The aqueous solution, which contains the expected phthalimide (80% of the theoretical amount), is treated, as in the above preparation, with hydrazine hydrate in order to give the expected amine II in a yield of 85%.

Chromatography: Superdex® 30 gel in a 16 mm/60 cm column (Pharmacia).

Eluent: 0.1M NaCl/0.05M $NaH_2PO_4$/0.01M $NaN_3$ pH=7.2;

Flow rate 1 ml/minute;

Elution volume: 102 ml for 1 mg in 250 μl.

Symmetry® C 18.5 μm HPLC column (Waters), l=25 cm, d=4.6 mm;

Eluent: $CH_3CN$/0.01M $KH_2PO_4$ (15/85) (without $CH_3CN$ for 5 minutes);

Flow rate 1 mil/min;

Retention time of the isomers: about 18 min.

Preparation of the amine of formula II with $R_1$=H, $R_1$=A, $R'_2$=$R'_2$=$CH_2(CHOH)_4CH_2OH$ and X=Br (Compound IId)

Step (a):

17.3 g of 5-phthalimidoacetamido-2,4,6-tribromoisophthaloyl dichloride are introduced, at 70° C., into 185 ml of dimethylacetamide, 11.3 ml of triethylamine and 66.6 g of compound IIb. After stirring for 24 hours, the medium, at room temperature, is poured into 2 liters of methylene chloride and the precipitate formed is separated out. It is purified by chromatography of its aqueous solution on 3 l of polystyrene resin, type XAD 1600, sold by Rohm and Haas. 90% yield.

Step (b):

A solution of 37.5 g of the compound isolated above in 130 ml of water and 2 ml of aqueous 35% hydrazine solution is maintained at 80° C. for 5 hours. After cooling, the medium is brought to pH 1 by addition of aqueous 10N HCl and is then chromatographed on 100 ml of Amberlite® cationic resin (IRN 77) and anionic resin (IRA 67) and on 500 ml of an acidic cation-exchange polystyrene resin of the type IMAC HP222 sold by Rohm and Haas, from which the desired product is eluted with aqueous 3M $NH_4OH$ solution and then isolated by precipitation from ethanol after concentration.

HPLC chromatography: LiChrospher® 100 RP18, 5.25 μm column, l=25 cm, d=4 mm; (Merck), eluent: aqueous HCl (pH 3.4)/$CH_3CN$ 97/3; flow rate=1ml/min; retention time: 4.5 to 8 min.

Mass spectrum (electrospray): in agreement.

Preparation of the amine of formula II in which $R_1$=$CH_3$, $R_2$=$CH_2(CHOH)_2CH_2OH$ and X=I (Compound IIe)

Step (a):

25 g of 5-phthalimidoacetamido-2,4,6-triiodo-isophthaloyl dichloride are dissolved in 170 ml of dimethylacetamide at room temperature with 13 g of 4-(N-methyl) aminobutane-1,2,3-triol and 22.8 ml of tributylamine; the medium is kept stirring at room temperature for 8 hours and is then concentrated under reduced pressure. The residue is purified by chromatography of its aqueous solution on Amberlite® IRN 77 cationic $H^+$ resin. Yield >95%.

Step (b):

75 g of the product obtained above are introduced, at 80° C., into 50 ml of water containing 1.43 ml of aqueous 35% hydrazine solution and the mixture is maintained at this temperature for 5 hours, after which it is brought to pH 1 by addition of aqueous 10N HCl. The precipitate is separated out and the aqueous phase is chromatographed on 100 ml of Amberlite® IRC 50 cationic $H^+$ resin and then on 200 ml of Amberlite® IRA 67 anionic $OH^-$ resin.

By concentration, the final product is obtained in a yield of 80%.

TLC: on Merck 60 F silica plate; ethyl acetate/isopropanol/15N aqueous ammonia solution (35/35/40) as eluent. Rf=0.7.

EXAMPLE 1

Compound of formula I in which M=Na and

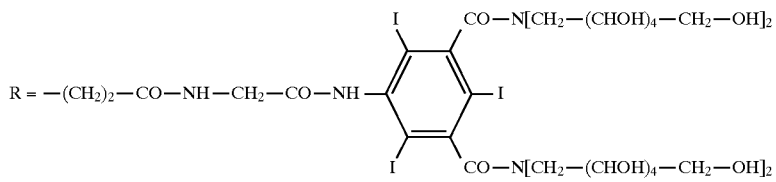

1 g of the gadolinium complex of formula III, 5 g of compound IIa and 6.8 g of 1-(3-dimethyl-aminopropyl)-3-ethylcarbodiimide hydrochloride in 13 ml of water are maintained at room temperature for 48 hours with stirring; the pH of the reaction medium is maintained at 7 by several additions of aqueous 1N HCl solution.

The reaction medium, to which 50 ml of water was added, is subjected to ultrafiltration with a nova type minisette cassette sold by the company Filtron (USA) containing a polyether sulphone membrane with a cutoff threshold of 5 KDa.

2 g of crude product are obtained in the form of the sodium salt, which can be purified by steric exclusion chromatography on a column of Superdex® gel, sold by Pharmacia, eluting with water.

HPLC chromatography: Hibar Licrosorb® Diol 5 μm column, l=25cm, d=4 mm (Merck)
Eluent: 0.01M $KH_2PO_4/CH_3CN$ (45/55)
Flow rate 1 ml/min
Retention time: 6 minutes

EXAMPLE 2

Compound of formula I in which M=Na and $$R = -(CH_2)_2-CO-NH-CH_2-CO-NH-\underset{Br}{\overset{Br}{\underset{|}{\bigcirc}}}\overset{CO-N[CH_2-(CHOH)_4-CH_2-OH]_2}{\underset{CO-N[CH_2-(CHOH)_4-CH_2-OH]_2}{-Br}}$$

50 g of 1-(3-dimethylaminopropyl)-3-ethyl-carbodiimide are introduced portionwise into a solution of 7.4 g of the gadolinium complex of formula III and 37 g of amine IIb in 100 ml of water, while maintaining the medium at pH 7 by addition of 1 N HCl. After stirring for 48 hours at room temperature, the medium is subjected to ultrafiltration, as in Example 1, but with a membrane with a cutoff threshold of 3 KDa, after which it is placed in contact with 500 ml of Amberlite® IRA 458 anionic ion-exchange resin (strong base).

After removal of the resin and evaporation of the water, 14 g of the expected product are obtained in the form of a beige-coloured solid.

The crude product can also be isolated from the reaction medium by precipitation from ethyl alcohol.

Chromatography: Hibar Licrosorb® Diol 5 μm HPLC column, l=25 cm, d=4 mm;
0.01M $KH_2PO_4/CH_3CN$ (45/55—v/v) as eluent;
Flow rate 1 ml/min;
Retention time: 5 minutes.

EXAMPLE 3

Compound of formula I in which M=Na and $$R = -(CH_2)_2-CO-NH-CH_2-CO-NH-\bigcirc-CO-NH-CH_2-CO-NH-\bigcirc$$

(with substituents I and $CO-N[CH_2-(CHOH)_4-CH_2-OH]_2$ on the aromatic rings)

0.3 g of the gadolinium complex of formula III and 3.5 g of compound IIc are dissolved in 10 ml of water and 1N HCl solution is introduced dropwise to pH 6.5, followed by addition of 1.1 g of 1-(3-dimethyl-aminopropyl)-3-ethylcarbodiimide hydrochloride.

After stirring for 24 hours at room temperature, 80 ml of water are added and the medium is purified as above, by ultrafiltration with a membrane having a cutoff threshold of 8 KDa, in order to isolate 1.5 g of the sodium salt of the expected complex in the form of a white powder.

The reaction can also be carried out at about 40° C., optionally in the presence of a catalytic amount of sodium salt of (N-hydroxysuccinimidyl)-3-sulphonic acid.

The product can be purified by precipitation from isopropanol.

Steric exclusion chromatography: 4 columns, sold by Shodex (JP) under the references OH Pak SB-( )HQ 8 mm in diameter and 30 cm in length, mounted in series, filled with polyhydroxymethacrylate gel; exclusion limits relative to pullulan: $10^6$ kdaltons (SB-804); $10^5$ kdaltons (SB-803); $10^4$ kdaltons (SB-802-5); $10^4$ kdaltons (SB-802-5). Aqueous 0.16M NaCl/CH$_3$CN (70/30 v/v) as eluent; flow rate 0.8 ml/min; T=30° C. Retention time: 34.4 minutes.

EXAMPLE 4

Compound of formula I in which M=Na and

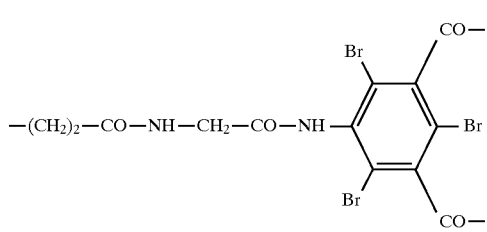
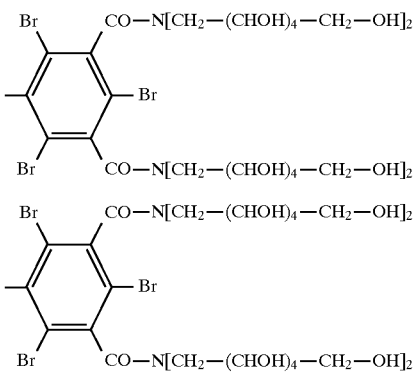

1.8 g of a sodium salt of the complex of formula III and 21.8 g of the amine (compound IId) are dissolved in 45 ml of water; after acidification with aqueous 1N HCl to pH 6, the medium is brought to 40° C. and 2.2 g of 1-(3-dimethylaminopropyl)-3-ethylcarbo-diimide hydrochloride and 0.165 g of a sodium salt of (N-hydroxysuccinimidyl)-3-sulphonic acid are intro-duced. After stirring for 2 hours, the mixture is poured into 600 ml of ethanol and the precipitate formed is dissolved in 270 ml of water.

The solution is ultrafiltered as above on a membrane with a cutoff threshold of 1 kdalton. After evaporation of the water, 15 g of the expected product are obtained in the form of a white powder.

Steric exclusion chromatography: same conditions as in Example 3. Retention time: 33.7 minutes.

EXAMPLE 5

Compound of formula I in which M=Na

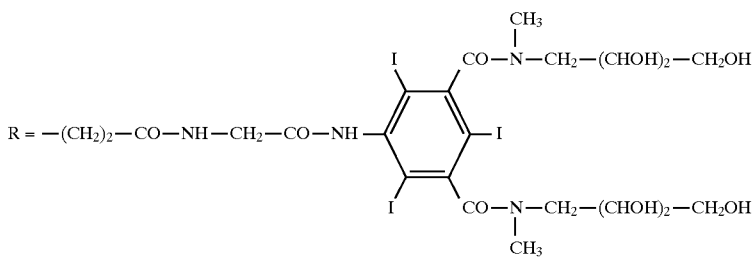

By applying the procedure of Example 1, starting with the amine IIe and the complex of formula III (sodium salt), the desired product is obtained.

HPLC: operating conditions of Example 2. Retention time: 3 minutes.

We claim:

1. Gadolinium complex of formula:

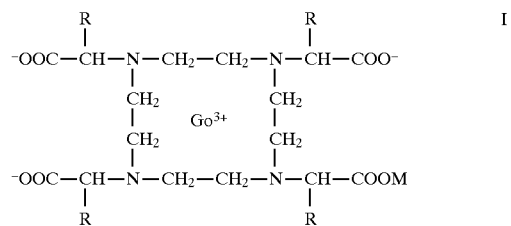

in which

R represents a group of formula:

—(CH$_2$)$_2$—CO—NH—CH$_2$—CO—NH— 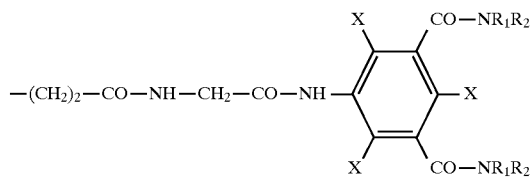

in which X is Br or I,

R$_1$ is selected from the group consisting of H, (C$_1$–C$_3$) alkyl or (C$_2$–C$_8$)mono- or polyhydroxyalkyl and R$_2$ is selected from the group consisting of (C$_2$–C$_8$) mono- or polyhydroxyalkyl, or alternatively R$_1$ is H and R$_2$ is a group of formula:

—CH$_2$—CO—NH— 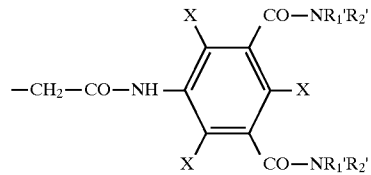 A

X being as defined above, and

R'$_1$ and R'$_2$ taken, independently of each other, any one of the meanings given for R$_1$ and R$_2$, with the exception of A, provided that —CO—NR$_1$R$_2$ or —CO—NR'$_1$R'$_2$ comprises at least 2 hydroxyl groups, and M represents H or the cation of an inorganic or organic base.

2. Complex according to claim 1, of formula I, in which —CONR$_1$R$_2$ or —CONR'$_1$R'$_2$ comprises at least 6 hydroxyl groups.

3. Complex according to claim 1 of formula I, in which M is an organic or inorganic cation selected from the group consisting of Na$^+$ and cations derived from lysine, arginine, N-methylglucamine or diethanolamine.

4. Complex according to claim 1 of formula I, in which R$_1$ and R$_2$ represent CH$_2$—(CHOH)$_4$—CH$_2$OH and X represents Br.

5. Complex according to claim 1 of formula I, in which R$_1$ is H, R$_2$ is A and R'$_1$ and R'$_2$ represent CH$_2$—(CHOH)$_4$—CH$_2$OH and X represents Br.

6. Contrast agent composition for magnetic resonance imaging, comprising a complex according to claim 1 in the form of a salt with a pharmaceutically acceptable base, in combination with a pharmaceutical vehicle.

7. Contrast agent composition for X-ray imaging, comprising a complex according to one of claim 1, in which X represents I, in the form of a salt with a pharmaceutically acceptable base, in combination with a pharmaceutical vehicle.

* * * * *

UNITED STATES PATENT AND TRADEMARK OFFICE
CERTIFICATE OF CORRECTION

PATENT NO. : 5,886,158

DATED : March 23, 1999

INVENTOR(S) : MEYER et al.

It is certified that error appears in the above-identified patent and that said Letters Patent is hereby corrected as shown below:

Title page, item [54] & Col. 1, the title should be changed to read --METAL COMPLEXES OF POLYAMINO ACIDS, AND THEIR UTILIZATION IN DIAGNOSTIC IMAGING--.

Signed and Sealed this

Ninth Day of November, 1999

Attest:

Q. TODD DICKINSON

Attesting Officer

Acting Commissioner of Patents and Trademarks